United States Patent [19]

Sugawara et al.

[11] 4,242,326

[45] Dec. 30, 1980

[54] ANTI-TUMOR SUBSTANCE AND PROCESS FOR PREPARING THE SAME

[75] Inventors: Yutaka Sugawara, Omiya; Akihiro Yamamoto, Higashiyamato; Mitsuaki Handa, Kamifukuoka; Hiroko Usami, Tokyo; Haruki Ogawa, Chofu, all of Japan

[73] Assignee: Chugai Seiyaku Kabushiki Kaisha, Tokyo, Japan

[21] Appl. No.: 49,744

[22] Filed: Jun. 18, 1979

Related U.S. Application Data

[63] Continuation of Ser. No. 783,270, Mar. 31, 1977, abandoned.

[30] Foreign Application Priority Data

Jun. 29, 1978 [JP] Japan ................................. 53/78039

[51] Int. Cl.$^3$ ............................................. A61K 35/74
[52] U.S. Cl. ..................................... 424/116; 435/68; 435/72; 435/101; 435/168; 435/169; 435/267; 435/272; 435/885
[58] Field of Search ................... 424/116; 435/68, 72, 435/101, 168, 169, 267, 272, 317, 885

[56] References Cited

U.S. PATENT DOCUMENTS

| | | | |
|---|---|---|---|
| 3,477,914 | 11/1969 | Okamoto et al. | 435/68 X |
| 3,632,746 | 1/1972 | Kono et al. | 424/93 |
| 3,729,554 | 4/1973 | Suzuki et al. | 424/93 |
| 3,786,141 | 1/1974 | Ogawa et al. | 435/272 X |
| 3,810,819 | 5/1974 | Okamoto et al. | 435/272 X |

FOREIGN PATENT DOCUMENTS 543227 12/1973 Switzerland .

*Primary Examiner*—Robert J. Warden
*Attorney, Agent, or Firm*—Browdy and Neimark

[57] ABSTRACT

An anti-tumor substance which is not only heatstable but also has low inflaming and pain-inducing properties and low pyrogenic activity is disclosed. The substance is prepared by disrupting cells of bacteria belonging to hemolytic streptococci, extracting from the disrupted material a water-insoluble substance and treating the substance with one or more proteases and, optionally, with one or more nucleases.

7 Claims, 2 Drawing Figures

4,242,326

ANTI-TUMOR SUBSTANCE AND PROCESS FOR PREPARING THE SAME

FIELD OF THE INVENTION

This invention relates to an anit-tumor substance extracted from cells of bacteria belonging to hemolytic streptococci and a process for preparing the substance.

BACKGROUND OF THE INVENTION

It has been known that living cells of bacteria belonging to hemolytic streptococci have a certain anti-cancer activity. However, because the activity is very unstable, many approaches have been tried to increase its stability. U.S. Pat. Nos. 3,477,914, 3,729,554 and 3,632,747 and Swiss Pat. No. 543,227 report various practicable methods wherein living cells of the bacteria are suspended in a saline solution containing an antibiotic such as penicillin, cephalosporin, cycloserine or the like, heated at a temperature ranging from 37° to 45° C. and, after adding a suitable stabilizer to the suspension, lyophilized to give dried preparations.

Although these preparations exhibit strong anti-tumor activities, they have defects for pharmaceutical preparation such that they induce pain in the place where administered to a patient, have inflaming property and induce transient fever in a patient upon administration.

On the other hand, various methods of extracting anti-tumor substances from the cells of bacteria belonging to hemolytic streptococci have been studied. Japanese Patent Publication No. 1647/63 reported a method which comprises disrupting the cells to recover the supernatant, adding an organic solvent to the supernatant and collecting the precipitating antibiotic substances. Further, U.S. Pat. No. 3,810,819 disclosed a method which comprises disrupting or lysing the cells to recover the supernatant and collecting active substances as a fraction containing 50–80% saturated ammonium sulfate solution. These anti-tumor substances recovered from the water-soluble fractions are comprised mainly of proteins and are extremely unstable against heat and are considerably lower in anti-tumor activity than a preparation containing cells. In addition, they have a high inflaming property and there is relatively high possibility to induce fever or pain in a patient upon administration.

Also, a method has been known from U.S. Pat. No. 3,786,141, which comprises having a lytic enzyme act on cells of the bacteria belonging to hemolytic streptococci and recovering water-insoluble active substances from the lysed solution. This type of substance comprises mainly protoplasmic membrane of the cells, and has essentially no inflaming property, pyrogenic activity or pain-inducing property. However, the anti-tumor activity of the object substance is unstable against heat.

During the study, the inventors have found that substances which were obtained by physically disrupting cells of bacteria belonging to hemolytic streptococci to recover a water-insoluble fraction mainly comprising cell wall components and by treating the fraction with a nuclease or protease, have low inflaming and pain-inducing properties and a strong anti-tumor activity with good stability against heat. The inventors have continued their studies based on such facts to complete this invention.

SUMMARY OF THE INVENTION

An object of this invention is to provide an anti-tumor substance with good stability against heat having low inflaming and pain-inducing properties.

Another object of this invention is to provide a process for preparing such anti-tumor substance which comprises physically disrupting cells of bacteria belonging to hemolytic streptococci, collecting the water-insoluble substances from the disrupted mixture, treating the substance with one or more protease or with a deoxyribonuclease, ribonuclease and one or more protease and, optionally, purifying the object substance by sucrose density gradient method.

DETAILED DESCRIPTION OF PREFERRED EMBODIMENTS

Figure 1:
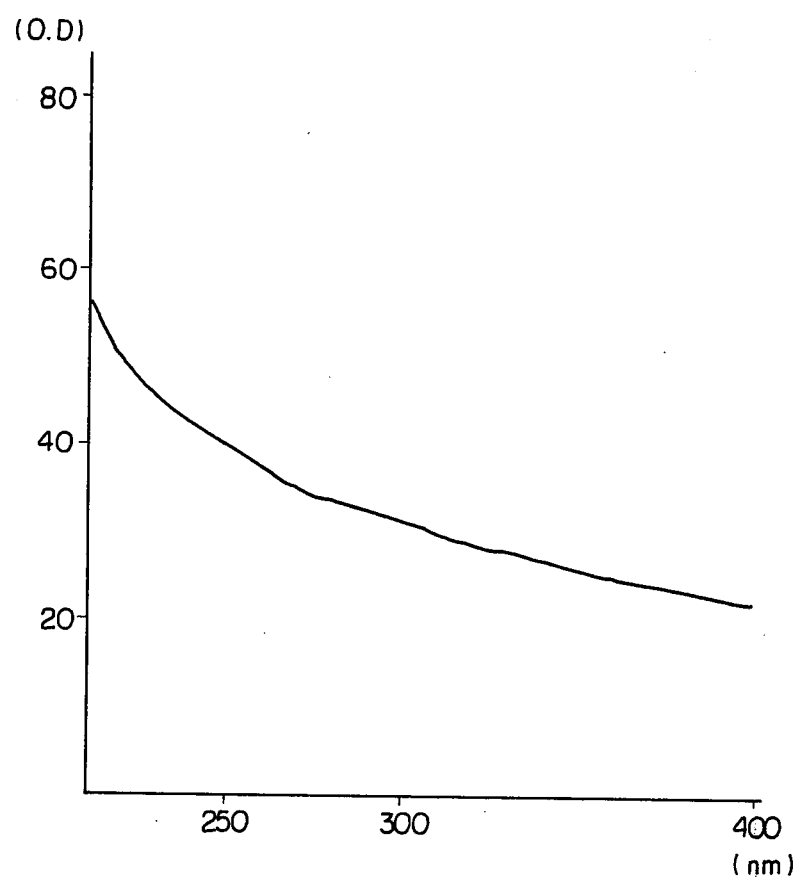

This invention will be explained hereunder in more detail. The cells of bacteria belonging to hemolytic streptococci, such as *Streptococcus pyogenes* Su strain, *Streptococcus pyogenes* C 203 S strein, *Streptococcus pyogenes* S-43 strain, *Streptococcus pyogenes* Blackmore strain or *Streptococcus equisimilis,* which are obtained by cultivation are suspended in an appropriate saline such as physiological saline or the like, or in distilled water, and disrupted by physical means, for example, by the use of sonicator, Braun cell homogenizer or the like, or by grinding them in the presence of powdery alumina in a mortar. The suspension of disrupted cells is centrifuged first at a low rotation speed to remove undisrupted cells as precipitate and then the supernatant is centrifuged agains at a high rotation speed. The resulting precipitate is then recovered and washed with an appropriate saline or distilled water, and treated with a protease, such as proteinase, trypsin, pepsin, nagarse or the like and washed again with an appropriate saline or distilled water. The thus obtained material comprises cell wall components which can be used as an anti-tumor preparation by suspending in an appropriate medium. However, the material can be made more pure by treating it with a deoxyribonuclease and a ribonuclease and, optionally, further purifying the treated material by sucrose density gradient method.

The treatment with a nuclease or protease according to this invention is desirably carried out under optimal conditions for the specific enzyme used. For example, the treatment is carried out by suspending the substrate and the enzyme in an appropriate buffer such as a phosphate buffer or a glycine-hydrochloric acid buffer to adjust the pH to the optimal pH for the enzyme and treating at around 37° C. for a period ranging from several hours to several tens hours.

The anti-tumor substance according to the process of this invention, for example, by the process described in Example 1 is grayish white powder and has an elementary analysis value: N, 7.31%; C, 42.97%; and H, 5.64%. Ultraviolet absorption spectrum measured as a suspension in physiological saline, and infrared absorption spectrum (KB$_r$) are shown in charts in FIG. 1 and FIG. 2, respectively, attached to this specification.

The object substance is believed to be a protein combined with polysaccharides comprising rhamnose, hexosamine and others. Results of analysis of the chemical composition are shown in Table 1 below.

TABLE 1

| Component | Contents* (%) |
|---|---|
| rhamnose | 33.3 |

TABLE 1-continued

| Component | Contents* (%) |
|---|---|
| hexosamine | 12.7 |
| protein | 16.7 |
| total lipid | 0.2 |
| RNA | 0 |
| DNA | 0 |

*The rhamnose content was determined by Gibbon's method, hexosamine by Elson-Morgan method, protein by Laury's method, whole lipid by a method comprising extracting with chloroform-methanol (3:1) and weighing the dryed extract, RNA by the orcinol reaction and DNA by the indole reaction.

Although the anti-tumor substance of this invention is stable against heat and can be stored for a long time in the form of a suspension, in contrast to a preparation containing cells of hemolytic streptococci, the substance can be suspended in an appropriate medium and then lyophilized.

This invention is further illustrated by the following Experiments and Examples, but it should not be construed that these Experiments and Examples limit the scope of this invention.

EXPERIMENT 1

Sarcoma 180 tumor cells were subcutaneously inoculated in the inguinal region of male ICR mice (4 weeks old) in a count of $3 \times 10^6$ cells per mouse. Twenty-four hours after the inoculation, each mouse was subcutaneously injected in the belly every day for 4 days with the anti-tumor preparation of this invention, the preparation of this invention which had been heated at 90° C. for 30 minutes or the preparation referred to as OK-432 as a positive control. The OK-432 preparation was prepared by treating cells of *Streptococcus pyogenes* Su strain with penicillin and lyophilizing them. Fourteen days after the inoculation of the tumor cells, the grown tumor of each mouse was excised and weighed. For the control, physiological saline was used instead of the above preparation.

The results are shown in Table 2.

TABLE 2

| Type of Preparation | Dose* μg/mouse | Number of the Test Animal (heads) | Average Tumor Weight (mg) | Suppression (%) |
|---|---|---|---|---|
| Preparation of Example 1 | 3.6 | 10 | 567 | 47.3 |
| Preparation of Example 2 | 3.2 | 10 | 613 | 43.1 |
| Preparation of Example 3 | 3.0 | 10 | 658 | 38.9 |
| Preparation of Example 4 | 2.7 | 10 | 635 | 41.0 |
| Heat-treated Preparation of Example 1 (90° C. about 30 minutes) | 3.6 | 10 | 600 | 44.2 |
| OK-432 | 50.0 | 10 | 554 | 48.5 |
| Physiological Saline | — | 10 | 1076 | — |

*Dose of each preparation corresponds to an amount prepared from 50 μg of dry cells.

As is clearly shown in Table 2, the anti-tumor activity of the preparations of this invention was almost equivalent to that of OK-432 and the preparation of this invention was stable against heat.

EXPERIMENT 2

Mastocytoma P-815 tumor cells were subcutaneously inoculated in the inguinal region of male $BDF_1$ mice (5 weeks old, 10 mice per test group) in a count of $2.5 \times 10^4$ cells per mouse. Twenty-four hours after the inoculation, each mouse was intravenously administered every day for 4 days the anti-tumor preparation obtained by Example 1 or OK-432 as a positive control. The dimensional change of the tumor with passage of time was measured over the skin, and recorded in terms of $\sqrt{\text{longest diameter} \times \text{shortest diameter}}$. As a control, physiological saline was used instead of the preparations.

The results are shown in Table 3.

TABLE 3

| | | Dimension of Tumor | | | |
|---|---|---|---|---|---|
| | | 15 days after | | 23 days after | |
| Type of Preparation | Dose (μg/ mouse) | Average ± S.E.*** | Suppression (%) | Average ± S.E. | Suppression (%) |
| Preparation of Example 1 | 14.4* | 4.0 ± 3.7 | 41 | 6.9 ± 5.1 | 44 |
| | 7.2** | 4.4 ± 2.5 | 35 | 4.7 ± 4.1 | 61 |
| OK-432 | 100* | 2.6 ± 2.5 | 62 | 5.0 ± 3.3 | 59 |
| Physiological Saline | — | 6.8 ± 0.3 | — | 12.3 ± 2.7 | — |

*Dose corresponds to an amount prepared from 200 μg of dry cells.
**Dose corresponds to an amount prepared from 100 μg of dry cells.
***S.E.: Standard errors As is clear from the data in Table 3, the preparation obtained in Example 1 also exhibited remarkable anti-tumor activity against the P-815 tumor.

EXPERIMENT 3

In this Experiment, the strong action of the anti-tumor preparation of this invention for amplifying the induction of immunity against mouse leukemia L1210 cells was confirmed. A suspension of L1210 cells ($6 \times 10^7$ cells/ml) was mixed with an equivalent volume of 8 mM sodium iodoacetate solution and allowed to stand at 37° C. for 20 minutes to obtain the treated cells (referred to as IA-L1210 hereunder). Female $BDF_1$ mice (8 weeks old) were divided into groups of 5 members each and subcutaneously injected with the IA-L1210 cells in a count of $5 \times 10^6$ per mouse (first sensitization) and, 10 days after the first sensitization, the injection was repeated (the additional sensitization). The test mice were subcutaneously administered the preparation of this invention or OK-432 as a positive control twice at the same times as the first and the additional sensitizations. Five days after the additional sensitization, native L1210 cells were inoculated subcutaneously in the test mice in a count of $10^4$ cells/mouse and their percent survival was observed.

As controls, one group of mice was administered only with IA-L1210 and another group of mice was not sensitized.

The results are shown in Table 4 below.

TABLE 4

| Sensitization (Twice) | Type of Preparation (Total Dose: μg/head × 2) | Mean Survival Days | ILS* (%) | Number of Survival Animals 40 days after L1210 Inoculation |
|---|---|---|---|---|
| IA-L1210 | Preparation of Example 1 (7.2) | 38.8 | 62 | 4 |
|  | Preparation of Example 1 (7.2) | 37.4 | 56 | 4 |
|  | OK-432 (100) | 37.6 | 57 | 4 |
|  | — | 25.4 | 6 | 1 |
| — | — | 24.0 | — | 0 |

*ILS = $\frac{T - C}{C} \times 100$

T = Mean survival days for group of treated mice
C = Mean survival days for group of untreated mice.

EXPERIMENT 4

The anti-tumor preparation obtained according to this invention remarkably reduced pain-inducing and inflaming properties in comparison with those of OK-432.

Male ICR mice (5 weeks old, ten mice per group) were intraperitoneally administered the preparation of this invention in a dose of 25 μg per mouse. During the 60 minutes following the administration no abnormal movement was observed. In contrast the mice which had been administered OK-432 in a dose of 100 μg/mouse on the basis of weight of dry cells exhibited various levels of the so-called writhing syndrome, particularly, twisting of the body or stretching hind legs, caused by the induction of pain.

On the other hand, male ICR mice (5 weeks old; 5 mice per group) were intracutanesouly injected in the back with the anti-tumor preparation of this invention in a dose of 25 μg/mouse or with OK-432 in a dose of 100 μg/mouse on the basis of weight of dry cells and, 3 hours after the injection, intravenously injected in the tail vein with a 0.5% Evans blue solution. Thirty minutes after the injection of the dye, the mice were sacrificed, the skin of the injected portion in the back was peeled and the leakage of the dye in that portion was observed.

The results are shown in Table 5 below.

TABLE 5

| Type of Preparation | Dose (μg/head) | Dye-leaked animal (head) / Total test animal (head) |
|---|---|---|
| Preparation of Example 1 | 25 | 0/5 |
| Preparation of Example 2 | 25 | 0/5 |
| Preparation of Example 3 | 25 | 0/5 |
| Preparation of Example 4 | 25 | 0/5 |
| OK-432 | 100 | 5/5 |

As is clear from Table 5, the dye leakage in the mice administered with OK-432 was positive, while none of the mice administered the anti-tumor preparation of this invention exhibited the dye leakage. These results confirm the low inflaming property of the preparation of this invention.

EXAMPLE 1

*Streptococcus pyogenes* Su-strain (ATCC 21060) was inoculated in bouillon medium (1500 ml) and cultivated for 20 hours. The whole culture broth was then inoculated in 3% yeast extract medium (30 l) and statically cultivated at 37° C. for 20 hours. The 3% yeast extract medium had been prepared by dissolving yeast extract in water, adjusting its pH to 7.4 with aqueous sodium hydroxide, heating the solution at 100° C. for one hour and, after cooling, removing the resulting precipitate by filtration and sterilizing the filtrate by exposing it to steam at 120° C. under a pressure of 1 kg/cm$^2$ for 10 minutes. The culture broth was cooled with ice and the cells in the broth were collected by centrifugation under cooling, washed twice with cold physiological saline, and suspended in BBM, the composition of which was 675 ml of maltose, 6 ml of 20% $KH_2PO_4$ aqueous solution having a pH of 6.9–7.0 adjusted with sodium hydroxide, 12 ml of a 2% $MgSO_4 7H_2O$ aqueous solution and 66 ml of distilled water. The suspension was mixed with 180 g of fine glass particles having an average diameter of 0.1 mm and, after dividing six aliquots, each aliquot of the mixture was subjected to Braun cell homogenizer (manufactured by B. Braun Melusungen) at about 4,000 rpm for 5 minutes to disrupt the cells. The resulting suspension was decanted to remove most of the glass particles and centrifuged at 1,500 rpm for 10 minutes to remove the precipitated glass particles and undisrupted cells. The supernatant was centrifuged again at 13,000 rpm for 30 minutes, and the precipitate was collected, washed twice with cold physiological saline and suspended in 300 ml of 50 mM phosphate buffer (pH, 7.0). The suspension was heated at 95° C. for 15 minutes and after cooling, centrifuged at 1,000 rpm for 10 minutes. The supernatant was centrifuged again at 13,000 rpm for 30 minutes and the resulting precipitate was suspended in 300 ml of 50 mM phosphate buffer. To the suspension were added 15 mg of deoxyribonuclease (820 Knitz u/mg, Sigma Chemical Co., U.S.A.) and 3 mg of ribonuclease (67 Knits u/mg, Sigma Chemical Co.) and the mixture was incubated at 37° C. for 2 hours. Then the mixture was centrifuged at 13,000 rpm for 30 minutes and the resulting precipitate was collected, suspended in 300 ml of 50 mM phosphate buffer (pH, 7.0), and, after adding 90 mg of pronase-E (Kaken Kagaku Kabushiki Kaisha, Japan), incubated at 37° C. for 24 hours.

The reaction mixture was centrifuged at 13,000 rpm for 30 minutes and the precipitate was suspended in 300 ml of 50 mM phosphate buffer (pH, 7.0) and, after adding 39 mg of crystalline chymotripsin (Sigma Chemical Co.), incubated at 37° C. for 2 hours. The mixture was centrifuged at 13,000 rpm for 30 minutes. The precipitate was recovered, suspended in 300 ml of 0.2 M glycine-HCl buffer (pH, 2.0) and, after the addition of 30 mg of pepsin (Sigma Chemical Co.) incubated at 37° C. for 2 hours. The mixture was centrifuged at 13,000 rpm for 30 minutes. The resulting precipitate was suspended in 28 ml of 5 mM phosphate buffer. Layers of sucrose aqueous solutions (4 ml each) each of which had a different specific gravity of 1.30, 1.25, 1.15 or 1.10, were placed from bottom to top in a centrifuge tube having a volume of 40 ml and then 4 ml layer of the suspension prepared above was placed on top of the layers of the sucrose solutions. After centrifigugation at 3,000 rpm for 70 minutes, the middle layers were collected by pipet and centrifuged at 13,000 rpm for 30 minutes. The precipitate (0.63 g as dry basis) was collected and washed twice by centrifugation with 50 mM phosphate buffer (pH, 7.0) then suspended in 100 ml of 50 mM phosphate buffer (pH, 7.0) to give an anti-tumor preparation.

EXAMPLE 2

Example 1 was repeated except that *Streptococcus pyogenes* C 203 S strain (ATCC 21546) was used instead of the Su strain to give an anti-tumor preparation (0.56 g as dry basis).

EXAMPLE 3

Example 1 was repeated except that *Streptococcus pyogenes* S-43 strain (ATCC 21547) was used instead of the Su strain to give an anti-tumor preparation (0.53 g as dry basis).

EXAMPLE 4

Example 1 was repeated except that *Streptococcus pyogenes* Blackmore strain (ATCC 21548) was used instead of the Su strain to give an anti-tumor preparation (0.47 g as dry basis).

EXAMPLE 5

Example 1 was repeated except that *Streptococcus equismilis* (being deposited with ATCC under Group-C' Streptococcus sp. ATCC 21597) was used instead of the Su strain to give an anti-tumor preparation (0.54 g as dry basis).

Figure 2:
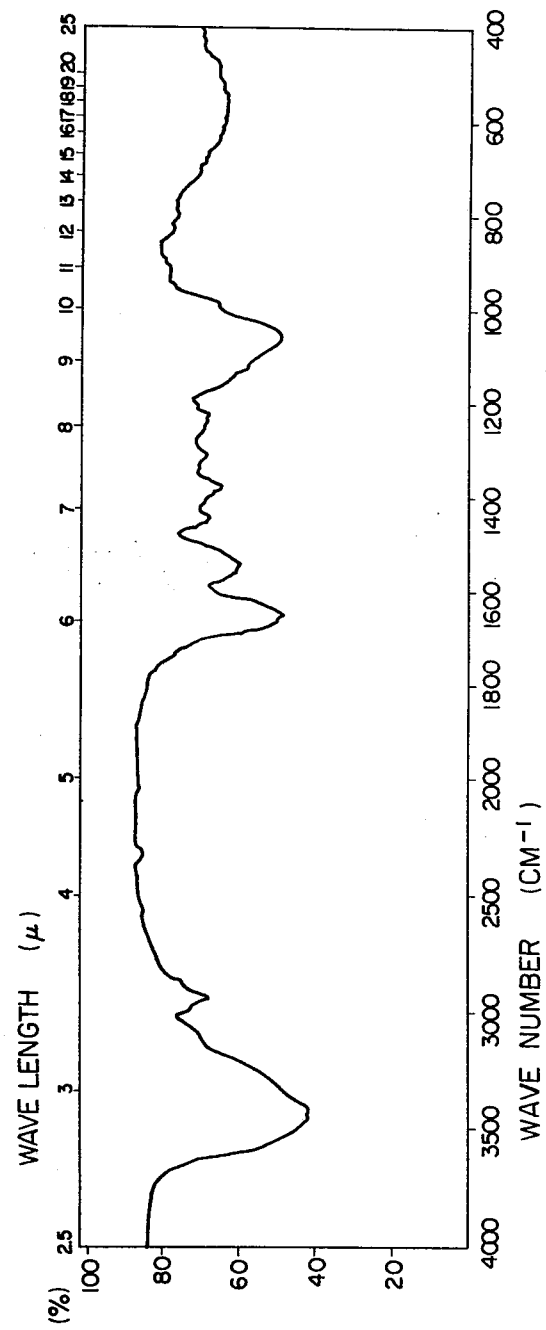

We claim:

1. A substance having the following properties:
   (a) appearance: from white to grayish white powder
   (b) solubility: insoluble in water
   (c) elemental analysis: C, 42.97%; H, 5.64%; N, 7.31%
   (d) ultraviolet absorption spectrum: as shown in FIG. 1
   (e) infrared absorption spectrum: as shown in FIG. 2
   (f) chemical composition: rhamnose, 33.3%; hexosamine, 12.7%; protein, 16.7%; total lipid, 0.2%, RNA, none; DNA, none.

2. A process for preparing the substance of claim 1 which comprises disrupting cells of bacteria belonging to hemolytic streptococci, extracting from the disrupted material a water-insoluble substance and digesting the substance with one or more protease.

3. A process according to claim 2 wherein said protease is selected from the group consisting of proteinase, trypsin, pepsin and nagarse.

4. A process according to claim 2 wherein said bacteria belonging to hemolytic streptococci are selected from the group consisting of *Streptococcus pyogenes* Su strain, ATCC 21060, *Streptococcus pyogenes* C 203 S strain, ATCC 21546, *Streptococcus pyogenes* S-43 strain, ATCC 21547, *Streptococcus pyogenes* Blackmore strain, ATCC 21548, and *Streptococcus equisimilis* ATCC 21597.

5. A process for preparing the substance of claim 1 which comprises disrupting cells of bacteria belonging to hemolytic streptococci, extracting from the disrupted material a water-insoluble substance and digesting the substance with deoxyribonuclease, ribonuclease and one or more proteases.

6. A process according to claim 5 wherein said protease is selected from the group consisting of proteinase, trypsin, pepsin and nagarse.

7. A process according to claim 5 wherein said bacteria belonging to hemolytic streptococci are selected from the group consisting of *Streptococcus pyogenes* Su strain, ATCC 21060, *Streptococcus pyogenes* C 203 S strain, ATCC 21546, *Streptococcus pyogenes* S-43 strain, ATCC 21547, *Streptococcus pyogenes* Blackmore strain, ATCC 21548, and *Streptococcus equisimilis*, ATCC 21597.

* * * * *